United States Statutory Invention Registration [19]

[11] Reg. Number: H875

Ellar et al. [43] Published: Jan. 1, 1991

[54] **TOXIN-ENCODING NUCLEIC ACID FRAGMENTS DERIVED FROM A *BACILLUS THURINGIENSIS* SUBSP. ISRAELENSIS GENE**

[75] Inventors: David J. Ellar; Elizabeth S. Ward, both of Cambridge, England

[73] Assignee: E. I. Du Pont de Nemours and Company, Inc., Wilmington, Del.

[21] Appl. No.: 170,211

[22] Filed: Mar. 18, 1988

[51] Int. Cl.[5] ..... C12P 19/34; C12P 21/06; C12N 15/00

[52] U.S. Cl. ..... 435/91; 435/69.1; 435/172.3; 435/252.31; 435/252.5; 435/320; 435/832; 530/350; 530/858; 935/27; 935/60; 536/27

[58] Field of Search ..... 435/68, 70, 172.3, 252.3, 435/320, 252.31, 252.33; 536/27; 938/9, 10; 530/300

[56] References Cited

U.S. PATENT DOCUMENTS 4,652,628 3/1987 Walfield et al. .
4,771,131 9/1988 Herrnstadt et al. ..... 536/27

OTHER PUBLICATIONS

Rastetter, W. H. 1983. Trends in Biotechnol. 1, 80–84.
Campbell et al. 1987, TIBTGECH 5, 302–306.
Goldberg, et al., *Mosquito News,* 37: 355–358 (1977).
de Barjac et al., *CR Acad. Sci. Paris,* Ser D 286: 797–800 (1978).
Thomas, et al., *FEBS Letters,* 154: 362–368 (1983).
Thomas, et al., *J. of Cell Sci.,* 60: 181–197 (1983).
Davidson et al., *Curr. Microbiol.,* 11: 171–174 (1984).
Armstrong, et al., *J. Bacteriol.,* 161 : 39–46 (1985).
Wu et al., *FEDS Letts.,* 190 : 232–236 (1985).
Lee et al., *Biochem. Biophys. Res. Commun.,* 126: 953–960 (1985).
Hurley et al., *Biochem. Biophys. Res. Commun., 126 : 961–965 (1985).*
Sriram et al., *Biochem. Biophys. Res. Commun.,* 132: 19–27 (1985).
Cheung et al., *Curr. Microbiol.,* 12 : 121–126 (1985).
Ward et al., *FEDS Letts.,* 175 : 377–781 (1984).
Waalwijk et al., *Nucleic Acids Res.,* 13 : 8207–8217 (1985).
Bourgouin et al., *Mol. Gen. Genet.,* 205 : 390–397 (1986).
Ward et al., *J. Mol. Biol.,* 191: 1–11, 13–22 (1986).
Knowles et al., *Biochem. Biophys. Acta.,* 924 : 509–518 (1987).

*Primary Examiner*—Richard D. Lovering
*Assistant Examiner*—John M. Covert

[57] ABSTRACT

Novel nucleic acid fragments coding for insecticidal proteins, the insecticidal proteins encoded thereby, insecticidal compositions containing such proteins, and the use of these proteins in combatting insects, particularly mosquitoes, are described. Chimeric genes containing the novel nucleic acid fragments, and microorganisms, tissues, seeds, and plants incorporating the nucleic acid fragments are also discussed.

11 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

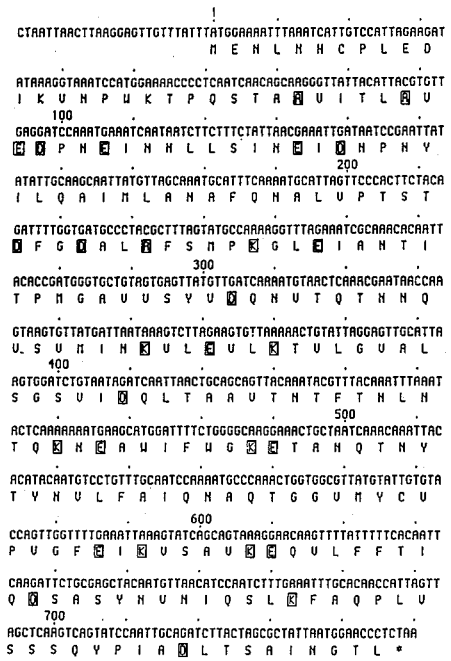

F I G. 1

```
                                  !
CTAATTAACTTAAGGAGTTGTTTATTTATGGAAAATTTAAATCATTGTCCATTAGAAGAT
                                  M  E  N  L  N  H  C  P  L  E  D

ATAAAGGTAAATCCATGGAAAACCCCTCAATCAACAGCAAGGGTTATTACATTACGTGTT
I  K  V  N  P  W  K  T  P  Q  S  T  A  R  V  I  T  L  R  V
     100
GAGGATCCAAATGAAATCAATAATCTTCTTTCTATTAACGAAATTGATAATCCGAATTAT
E  D  P  N  E  I  N  N  L  L  S  I  N  E  I  D  N  P  N  Y
                                                   200
ATATTGCAAGCAATTATGTTAGCAAATGCATTTCAAAATGCATTAGTTCCCACTTCTACA
I  L  Q  A  I  M  L  A  N  A  F  Q  N  A  L  V  P  T  S  T

GATTTTGGTGATGCCCTACGCTTTAGTATGCCAAAAGGTTTAGAAATCGCAAACACAATT
D  F  G  D  A  L  R  F  S  M  P  K  G  L  E  I  A  N  T  I
                          300
ACACCGATGGGTGCTGTAGTGAGTTATGTTGATCAAAATGTAACTCAAACGAATAACCAA
T  P  M  G  A  V  V  S  Y  V  D  Q  N  V  T  Q  T  N  N  Q

GTAAGTGTTATGATTAATAAAGTCTTAGAAGTGTTAAAAACTGTATTAGGAGTTGCATTA
V  S  V  M  I  N  K  V  L  E  V  L  K  T  V  L  G  V  A  L
     400
AGTGGATCTGTAATAGATCAATTAACTGCAGCAGTTACAAATACGTTTACAAATTTAAAT
S  G  S  V  I  D  Q  L  T  A  A  V  T  N  T  F  T  N  L  N
                                                   500
ACTCAAAAAAATGAAGCATGGATTTTCTGGGGCAAGGAAACTGCTAATCAAACAAATTAC
T  Q  K  N  E  A  W  I  F  W  G  K  E  T  A  N  Q  T  N  Y

ACATACAATGTCCTGTTTGCAATCCAAAATGCCCAAACTGGTGGCGTTATGTATTGTGTA
T  Y  N  V  L  F  A  I  Q  N  A  Q  T  G  G  V  M  Y  C  V
                          600
CCAGTTGGTTTTGAAATTAAAGTATCAGCAGTAAAGGAACAAGTTTTATTTTTCACAATT
P  V  G  F  E  I  K  V  S  A  V  K  E  Q  V  L  F  F  T  I

CAAGATTCTGCGAGCTACAATGTTAACATCCAATCTTTGAAATTTGCACAACCATTAGTT
Q  D  S  A  S  Y  N  V  N  I  Q  S  L  K  F  A  Q  P  L  V
     700
AGCTCAAGTCAGTATCCAATTGCAGATCTTACTAGCGCTATTAATGGAACCCTCTAA
S  S  S  Q  Y  P  I  A  D  L  T  S  A  I  N  G  T  L  *
```

TOXIN-ENCODING NUCLEIC ACID FRAGMENTS DERIVED FROM A *BACILLUS THURINGIENSIS* SUBSP. ISRAELENSIS GENE

BACKGROUND OF THE INVENTION

Field of the Invention

The present invention pertains to novel nucleic acid fragments coding for insecticidal proteins. More specifically, the invention relates to novel fragments encoding insecticidal proteins, said proteins having greater solubility characteristics, less haemolytic activity, and/or greater expression potential in certain specific cells, than the protein encoded by the wild type 27 kDa *Bacillus thuringiensis* var. israelensis gene, the encoded proteins, insecticidal compositions containing these proteins, and th use of these proteins in combating insects, particularly mosquitoes, are also contemplated in the subject invention. Chimeric genes containing the novel nucleic acid fragments, and microorganisms, plant cells, plant tissues, seeds and plants incorporating the nucleic acid fragments are further within the ambit of the present invention.

The spore-forming bacteria *Bacillus thuringiensis* var. israelensis produces a proteinaceous crystalline inclusion which is toxic to the larvae of *Mosquito News*, 37: 355–358 (1977); de Barjac et al., *CR Acad. Sci. Paris*, ser D 286: 797–800 (1978); Thomas, et al., *FEBS Letters*, 154: 362–368 (1983). The native var. israelensis crystal is irregular in shape and consists of several major polypeptides in addition to a number of other polypeptides which are present in minor amounts. See, Thomas et al., *J. of Cell Sci.*, 60: 181–197 (1983). A protein of molecular weight 27 kDa is the most prominent of these polypeptides, and its larvicidal and haemolytic properties have been studied using both purified preparations of the 27 kDa δ-endotoxin and a 25 kDa segment thereof. See, Davidson et al., Curr. *Microbiol.*, 11: 171–174 (1984); Thomas, W. E. , Ph.D., Thesis, University of Cambridge, "Biochemistry and Mode of Action of the Insecticidal δ-endotoxins of *Bacillus thuringiensis*" (1984); Armstrong, et al., J. Bacteriol., 161: 39–46 (1985); Wu et al., *FEBS Letts.*, 190: 232–236 (1985); Lee et al., *Biochem. Biophys. Res. Commun.*, 126: 953–960 (1985); Hurley et al., *Biochem. Biophys. Res. Commun.*, 126: 961–965 (1985); Sriram et al., *Biochem. Biophys. Res. Commun.*, 132: 19–27 (1985); and Cheung et al., *Curr. Microbiol.*, 12: 121–126 (1985).

Using a somewhat different approach to investigate the properties of this polypeptide, the gene encoding the 27 kDa δ-endotoxin has been cloned in both *Escherichia coli* (see, Ward et al., *FEBS Letts.*, 175: 377–781 (1984); Waalwijk et al., *Nucleic Acids Res.*, 13: 8201–8217 (1985); Bourgouin et al., *Mol. Gen. Genet.*, 205: 390–397 (1986), and in sporogenic and asporogenic strains of *Bacillus subtilis* (see, Ward et al., *J. Mol. Biol.*, 191: 1–11 (1986); Ward et al., *J. Mol. Biol.*, 191: 13–22 (1986)). In *E. coli*, induction of a high level of wild type 27 kDa δ-endotoxin expression has been found to have a significant deleterious effect on the growth of that bacterium. It has been postulated that the observed deleterious effect is due to binding of the toxin to phosphatidyl choline and phosphatidyl ethanolamine lipid receptors in *E. coli* cell plasma membranes. See, Ward, E. S., Ph.D. Thesis, University of Chambridge, "Molecular Genetics of an Insecticidal δ-endotoxin from *Bacillus thuringiensis* var. israelensis" (1988); Thomas, et al., *FEBS Letters*, 154: 362–368 (1983). In *B. subtilis* recombinants, the 27 kDa protein accumulates in the cytoplasm as phase bright crystalline inclusions, similar in appearance, but smaller than, the var. israelensis crystal. These inclusions have been purified and shown to consist entirely of 27 kDa δ-endotoxin. See, Ward et al., *J. Mol. Biol.*, 191: 1–11 (1986); Ward et al., *J. Mol Biol.*, 191: 13–22 (1986). Testing these inclusions in the absence of other crystal polypeptides, has shown this polypeptide to be both larvicidal and haemolytic. See, Ward et al., *J. Mol. Biol.*, 191: 1–11 (1986); Ward et al., *J. Mol. Biol.*, 191: 13–22 (1986). These results are consistent with those reported by Davidson et al., *Curr. Microbiol.*, 11: 171–174 (1984), Thomas, W. E., Ph.D. Thesis, University of Cambridge, "Biochemistry and Mode of Action of the Insecticidal δ-endotoxins of *Bacillus thuringiensis*" (1984), and Armstrong et al., *J. Bacteriol.*, 161: 39–46 (1985), but differ from those of several other groups who did not detect mosquitocidal activity in their preparations of this protein, such as Wu et al., *FEBS Letts.* 190: 232–236 (1985), Lee et al., *Biochem. Biohphys. Res. Commun.*, 126: 953–960 (1985), Hurley et al., *biochem. Biophys. Res. Commun.* 126: 961–965 (1985), and Cheung et al., *Curr. Microbiol.*, 12: 121–126 (1985).

The nucleotide sequence of the 27 kDa δ-endotoxin has been reported in the literature. See, Waalwijk et al., *Nucleic Acids Res.*, 13: 8207–8217 (1985); Ward et al., *J. Mol. Biol.*, 191: 1–11 (1986). the hytdropathyl plot of this protein shows it to be highly hydrophobic, and the protein has been shown to interact with specific plasma membrane phospholipids. See, Thomas et al., *FEBS Letts.*, 145: 362–368 (1983). It has also recently been shown by Knowles et al. *Biochem. Biophys. Acta.*, 924: 509–518 (1987) that this protein shares a common cytolytic mechanism with other *B. thuringiensis* δ-endotoxine from other serotypes. Commentators in this field have theorized that these δ-endotoxins bind to receptors on the membrane, and subsequently interact with the membrane to create a hole or pore. The generation of these pores is thought to lead to colloid-osmotic lysis, where an inflow of ions is accompanied by water influx, which in turn causes cell swelling followed by lysis. See, Knowles et al. *Biochem. Biophys. Acta.*, 924: 509–518 (1987).

The present invention is based on a more detailed understanding of the interaction of the var. israelensis 27 kDa δ-endotoxin with target membranes. Through in vitro mutagenesis techniques, specific codon alterations have been directed in the cloned δ-endotoxin gene. Various of the mutant proteins have been found to possess greater solubility characteristics, less haemolytic activity, and/or greater expression potential in cells containing significant amounts of phosphatidate-type toxin receptors, than the protein encoded by the wild type 27 kDa *Bacillus thuringiensis* var. israelensis gene.

SUMMARY OF THE INVENTION

The present invention relates to novel nucleic acid fragments coding for insecticidal proteins, insecticidal proteins encoded thereby, insecticidal compositions containing such proteins, and the use of such proteins in combating insects, particularly mosquitoes. Chimeric genes containing the novel nucleic acid fragments, and microorganisms, plant cells, plant tissues, seeds and plants incorporating the nucleic acid fragments are also within the ambit of the present invention.

In one aspect, the invention pertains to nucleic acid fragments coding for an insecticidal protein having greater solubility characteristics than the protein encoded by the wild type 27 kDa *Bacillus thuringiensis* var. israelensis gene.

More specifically, in its first aspect, the invention is directed to a nucleic acid fragment comprising a nucleic acid sequence encoding a soluble insecticidal protein, said soluble protein meeting at least one of requirements (a) to (c), but otherwise having sequence homology or substantial sequence homology to the amino acid sequence shown in FIG. 1 which begins with amino acid 1 and ends with amino acid 249, said requirements (a) to (c) being as follows:

(a) the nucleic acid fragment has a sequence which encodes an amino acid subsequence in FIG. 1 from amino acids 1 to 82 and 122 to 136 wherein at least one of the positively charged amino acids is instead a negatively charged or a neutral amino acid, or at least one of the neutral amino acids is instead a negatively charged amino acid;

(b) the nucleic acid fragment has a sequence which encodes an amino acid subsequence in FIG. 1 from amino acids 199 to 212 wherein the positively charged amino acid is instead a negatively charged or a neutral amino acid, or the negatively charged amino acid is at least one of the neutral amino acids is instead a positively charged or a negatively charged amino acid; and (c) the nucleic acid fragment has a sequence which encodes an amino acid subsequence in FIG. 1 from amino acids 226 to 249 wherein the negatively charged amino acid is instead a positively charged or a neutral amino acid, or at least one of the neutral amino acids is instead a positively charged amino acid.

Preferences, as they pertain to each of requirements (a) to (c) above, are as follows:

With respect to requirement (a), preferably the neutral amino acids remain unchanged, but at least one of the positively charged amino acids is instead a negatively charged or a neutral amino acid, even more preferably a neutral amino acid. The neutral amino acid is preferably alanine. The most preferred changes, with respect to requirement (a), include where arginine 25 is instead alanine 25, arginine 30 is instead alanine 30, arginine 78 is instead alanine 78 and/or lysine 124 is instead alanine 124.

With respect to requirement (b), preferably the neutral amino acids remain unchanged, but the positively charged amino acid is instead a negatively charged or a neutral amino acid, and/or the negatively charged amino acid is instead a positively charged or a neutral amino acid. Even more preferably, the positively charged amino acid is instead a neutral amino acid and/or the negatively charged amino acid is instead a neutral amino acid. The neutral amino acid is preferably alanine. The most preferred changes, with respect to requirement (b), include where lysine 203 is instead alanine 203 and/or glutamic acid 204 is instead alanine 204.

With respect to requirement (c), preferably the neutral amino acids remain unchanged, but the negatively charged amino acid is instead a positively charged or a neutral amino acid, more preferably a neutral amino acid. The neutral amino acid is preferably alanine. The most preferred change, with respect to requirement (c), is where aspartic acid 240 is instead alanine 240.

With respect to requirement (c), preferably the neutral amino acids remain unchanged, but the negatively charged amino acid is instead a positively charged or a neutral amino acid, more preferably a neutral amino acid. The neutral amino acid is preferably alanine. The most preferred change, with respect to requirement (c), is where aspartic acid 240 is instead alanine 240.

The most preferred nucleic acid fragments in the first aspect of the invention are those wherein:

only requirement (a) is met, and wherein, as the only change with respect to requirement (a), arginine 25 is instead alanine 25;

only requirement (a) is met, and wherein, as the only change with respect to requirement (a), arginine 30 is instead alanine 30;

only requirement (a) is met, and wherein as the only change with respect to requirement (a), arginine 78 is instead alanine 78;

only requirement (a) is met, and wherein as the only change with respect to requirement (a), lysine 124 is instead alanine 124;

only requirement (b) is met, and wherein as the only change with respect to requirement (b), lysine 203 is instead alanine 203;

only requirement (b) is met, and wherein as the only change with respect to requirement (b), glutamic acid 204 is instead alanine 204; and only requirement (c) is met, and wherein, as the only change with respect to requirement (c), aspartic acid 240 is instead alanine 240.

In a second aspect, the invention pertains to nucleic acid fragments coding for insecticidal proteins having less haemolytic activity than the protein encoded by the wild type 27 kDa *Bacillus thuringiensis* var. israelensis gene.

More specifically, in its second aspect, the invention is directed to a nucleic acid fragment comprising a nucleic acid sequence encoding an insecticidal protein having less haemolytic activity, said protein meeting at least one of requirements (a) to (g), but otherwise having sequence homology or substantial sequence homology to the amino acid sequence shown in FIG. 1 which beings with amino acid 1 and ends with amino acid 249, said requirements (a) to (g) being as follows:

(a) negatively charged glutamic acid 45 is instead a positively charged or a neutral amino acid;

(b) positively charged arginine 78 is instead a negatively charged or a neutral amino acid;

(c) positively charged lysine 154 is instead a negatively charged or a neutral amino acid;

(d) positively charged lysine 163 is instead a negatively charged or a neutral amino acid;

(e) negatively charged glutamic acid 164 is instead a positively charged or a neutral amino acid;

(f) negatively charged glutamic acid 204 is instead a positively charged or a neutral amino acid; and (g) positively charged lysine 225 is instead a negatively charged or a neutral amino acid.

Preferably, with respect to requirement (a), negatively charged glutamic acid 45 is instead a neutral amino acid, with respect to requirement (b), positively charged arginine 78 is instead a neutral amino acid, with respect to requirement (c), positively charged lysine 154 is instead a neutral amino acid, with respect to requirement (d), positively charged lysine 163 is instead a neutral amino acid, with respect to requirement (e), negatively charged glutamic acid 164 is instead a neutral amino acid, with respect to requirement (f), negatively charged glutamic acid 204 is instead a neutral amino acid, and with respect to requirement (g), positively charged lysine 225 is instead a neutral amino acid. The neutral amino acid is preferably alanine.

The most preferred nucleic acid fragments in the second aspect to the invention are those wherein:

only requirement (a) is met, and wherein with respect to requirement (a), negatively charged glutamic acid 45 is instead alanine 45;

only requirement (b) is met, and wherein with respect to requirement (b), positively charged arginine 78 is instead alanine 78;

only requirement (c) is met, and wherein with respect to requirement (c), positively charged lysine 154 is instead alanine 154;

only requirement (d) is met, and wherein with respect to requirement (d), positively charged lysine 163 is instead alanine 163;

only requirement (e) is met, and wherein with respect to requirement (e), negatively charged glutamic acid 164 is instead a neutral amino acid;

only requirement (f) is met, and wherein with respect to requirement (f), negatively charged glutamic acid 204 is instead a neutral amino acid; and only requirement (g) is met, and wherein with respect to requirement (g), positively charged lysine 225 is instead alanine 225.

In a third aspect, the invention pertains to nucleic acid fragments coding for insecticidal proteins having greater expression potential in cells containing significant amounts of phosphatidate-type toxin receptors than the protein encoded by the wild type 27 kDa *Bacillus thuringiensis* var. israelensis gene.

More specifically, in its third aspect, the invention is directed to a nucleic acid fragment comprising a nucleic acid sequence encoding an insecticidal protein having greater expression potential in cells containing significant amounts of phosphatidate-type toxin receptors, said protein meeting at least one of requirements (a) to (g), but otherwise having sequence homology or substantial sequence homology to the amino acid sequence shown in FIG. 1 which begins with amino acid 1 and ends with amino acid 249, said requirements (a) to (g) being as follows:

(a) negatively charged glutamic acid 45 is instead a positively charged or a neutral amino acid;

(b) positively charged arginine 78 is instead a negatively charged or a neutral amino acid;

(c) positively charged lysine 154 is instead a negatively charged or a neutral amino acid;

(d) positively charged lysine 163 is instead a negatively charged or a neutral amino acid;

(e) negatively charged glutamic acid 164 is instead a positively charged or a neutral amino acid;

(f) negatively charged glutamic acid 204 is instead a positively charged or a neutral amino acid; and (g) positively charged lysine 225 is instead a negatively charged or a neutral amino acid.

Preferably, with respect to requirement (a), negatively charged glutamic acid 45 is instead a neutral amino acid, with respect to requirement (b), positively charged arginine 78 is instead a neutral amino acid, with respect to requirement (c), positively charged lysine 154 is instead a neutral amino acid, with respect to requirement (d), positively charged lysine 163 is instead a neutral amino acid, with respect to requirement (e), negatively charged glutamic acid 164 is instead a neutral amino acid, with respect to requirement (f), negatively charged glutamic acid 204 is instead a neutral amino acid, and with respect to requirement (g), positively charged lysine 225 is instead a neutral amino acid. The neutral amino acid is preferably alanine.

The most preferred nucleic acid fragments in the third aspect of the invention are those wherein:

only requirement (a) is met, and wherein, with respect to requirement (a), negatively charged glutamic acid 45 is instead a neutral amino acid;

only requirement (b) is met, and wherein, with respect to requirement (b), positively charged arginine 78 is instead a neutral amino acid;

only requirement (c) is met, and wherein, with respect to requirement (c), positively charged lysine 154 is instead a neutral amino acid;

only requirement (d) is met, and wherein, with respect to requirement (d), positively charged lysine 163 is instead a neutral amino acid;

only requirement (e) is met, and wherein, with respect to requirement (e), negatively charged glutamic acid 164 is instead a neutral amino acid;

only requirement (f) is met, and wherein, with respect to requirement (f), negatively charged glutamic acid 204 is instead a neutral amino acid; and only requirement (g) is met, and wherein, with respect to requirement (g), negatively charged aspartic acid 213 is instead a positively charged or a neutral amino acid.

Preferably, the cells containing significant amounts of phosphatidate-type toxin receptors are *E. coli* cells.

The subject nucleic acid fragments in each of the three aspects of the invention code for insecticidal, particularly mosquitocidal, proteins as described above, and the present invention also pertains to these proteins. A preferred protein is one having a molecular weight of about 27 kDa. Insecticidal compositions comprising insecticidal amounts of such proteins and methods for controlling insects comprising applying to the locus to be protected an insecticidal amount of such proteins are also within the ambit of the present invention.

The invention further relates, in all three aspects, to microorganisms containing these novel nucleic acid fragments, and the use of these novel nucleic acid fragments to modify the properties or characteristics of microorganisms. With respect to the first aspect of the invention, the preferred microorganisms are *Bacillus magaterium, Bacillus subtilis* and *Bacillus thuringiensis*. The preferred microorganism in the second and third aspect to the invention is *Escherichia coli*.

In addition, in each aspect, the subject invention is directed to chimeric genes capable of expression in a microorganism or a plant cell comprising (1) a nucleic acid fragment which encodes an insecticidal protein as described above and (2) at least one nucleic acid fragment from a different source. Preferably the nucleic acid fragment from the different source is a promoter. The invention also pertains to microorganisms or plant cells containing such chimeric genes, and to plant tissues, seeds and plants which contain chimeric genes in one or more of their cells, and to the use of such chimeric genes to modify the properties and characteristic of microorganisms, plant cells, plant tissues, seeds and/or plants.

Preferably, the nucleic acid fragments of the present invention are DNA fragments. In addition, although the proteins encoded by the subject nucleic acid fragments may, other than with respect to any of the specified mutations which have been made, have either sequence homology or substantial sequence homology with the amino acid sequency shown in FIG. 1, preferably the proteins are otherwise homologous thereto.

BRIEF DESCRIPTION OF THE FIGURE

FIG. 1 shows illustrates the nucleotide sequence of the non-coding strand of the var. israelensis 27000 Da δ-endotoxin gene. The amino acid sequence corresponding to the structural gene is shown below the corresponding nucleotide sequence. The amino acids which have been altered by specific nucleic acid changes and tested for insecticidal activity, ability to be expressed in a solubilized form, haemolytic activity, and/or expression potential in cells containing significant amounts of phosphatidate-type toxin receptors are indicated by a surrounding box.

DETAILED DESCRIPTION OF THE INVENTION

In the present written description and/or claims, reference will be made to the following abbreviations, terms and phrases.

As used herein, the letter abbreviations C, G, A and T signify the nucleotides cytosine, guanine, adenine and thymine, respectively, found in DNA.

As used herein, amino acids are abbreviated as follows:

| | |
|---|---|
| A = Ala = alanine | R = Arg = arginine |
| N = Asn = asparagine | D = Asp = aspartic acid |
| C = Cys = cysteine | G = Gly = glycine |
| Q = Gln = glutamine | E = Glu = glutamic acid |
| H = His = histidine | K = Lys = lysine |
| I = Ile = isoleucine | L = Leu = leucine |
| M = Met = methionine | F = Phe = phenylalanine |
| P = Pro = proline | S = Ser = serine |
| T = Thr = threonine | W = Trp = tryptophan |
| Y = Tyr = tyrosine | V = Val = valine |

The abbreviations "bp" means base pair(s), "kb" means kilobase pairs and "kDa" means kilodalton.

The phrase "nucleic acid fragment(s)" as used herein includes single and double stranded deoxyribonucleic acid (DNA) and single stranded ribonucleic acid (RNA) segments, as applicable.

As used herein the phrases "sequence homology" or "homologous" denote a protein having the same amino acid sequence as another protein.

As used herein, the phrases "substantial sequence homology" or "substantially homologous" denote a protein having an amino acid sequence substantially similar to the sequence of another protein.

The terms "soluble" or "solubility", employed herein in connection with proteins expressed by the nucleic acid fragments of the first aspect of the present invention, denote proteins that when expressed, are partially or totally dissolved in the cellular fluids of the host.

"Expression potential" as employed herein means the ability to be produced in the host cell without significantly affecting the ability of the cell to grow and function.

The phrase "phosphatidate-type toxin receptors" signifies, as used herein, unsaturated phosphatidyl ethanolamine and unsaturated phosphatidyl choline lipids. Examples of cells which contain significant amounts of phosphatidate-type toxin receptors are *E. coli* and Pseudomonas, and other cells which have levels of phosphatidyl ethanolamine and phosphatidyl choline similar to *E. coli* and Pseudomonas. Such additional cells will be readily apparent to those skilled in the art.

The phrase "chimeric gene" as employed herein refers to a hybrid construct comprising (1) a nucleic acid fragment in accordance with the present invention which encodes an insecticidal protein and (2) at least one nucleic acid fragment from a different source. Preferably the nucleic acid fragment(s) from a different source comprises a promoter, although it can also include, for example, nucleic acid fragments from other *Bacillus thuringiensis* toxin genes of subspecies israelensis or other subspecies such as aizawai, kurstaki, etc.. Further suitable nucleic acid fragments from different sources will be readily apparent to those skilled in the art.

The term "promoter" herein refers to a DNA fragment, generally located upstream from the 5′ end of a coding sequence, which functions to facilitate transcription of the gene into mRNA by the enzyme RNA polymerase.

The term "microorganism", as used herein, includes unicellular organisms such as prokaryotes, e.g., Cyanophyta (blue green algae), or bacteria exemplified by Escherichia; lower eukaryotes, e.g., fungi exemplified by yeast and filamentous fungi such as Neurospora and Aspergillus, or algae exemplified by Rhodophyta, Phaeophyta and Chlorophyta; protists, e.g., amoebae, protozoa; and viruses, e.g., baculoviruses or nuclear polyhedrosis viruses.

The term "plant cell" as used herein denotes a cell from a multicellular higher plant, whether in a whole plant or in culture.

The term "plant tissue", as used herein denotes differentiated and undifferentiated plant cells, including not limited to roots, shoots, tumor tissue, such as crown galls, pollen, etc., whether in a whole plant or in culture.

The term "insecticidal", when used alone or in combination with other terms herein, means toxic (lethal) or combative (sublethal) to insects.

The novel insecticide-encoding nucleic acid fragments of the present invention may be obtained from a starting material of wild type *Bacillus thuringiensis* subsp. israelensis using the techniques of genetic engineering, molecular cloning and mutageneis described herein and variations thereof. Suitable variations on such techniques will be readily apparent to those skilled in the art. For general references on engineering and cloning procedures, see Maniatis et al., "Molecular Cloning: A Laboratory Manual" (Cold Spring Harbon, 1982). A strain of wild type *Bacillus thuringiensis* subsp. israelensis carrying a wild type 27 kDa gene has been deposited with the National Collections of Industrial & Marine Bacteria, Ltd., Torry Research Station, P.O. Box No. 31, 135 Abbey Road, Aberdeen AB9 8DG Scotland, and bears the deposit accession number NCIB 12699. It should also be noted that *Bacillus thuringiensis* subsp. morrisoni PG14 contains a 27 kDa gene which produces a protein quite substantially homologous to the 27 kDa gene product of subsp. israelensis, the encoded protein showing only a single amino acid difference. See, Earp et al., *Nucleic Acids Research,* 15: 3619 (1987). This would provide a further suitable starting material for the present invention.

In one aspect, the invention pertains to nucleic acid fragments coding for insecticidal proteins having greater solubility characteristics than the protein encoded by the wild type 27 kDa *Bacillus thuringiensis* var. israelensis gene.

The greater solubility characteristics of such proteins opens up possibilities for this gene which were heretofore not practicably contemplated. As one example, the ability to manipulate the gene to produce an insecticidal protein in a form which does not spontaneously aggregate in the producer organisms into crystalline inclusions gives rise to the possibility of utilizing a continuous fermentation process in which the protein is secreted by the producer organism and removed from the fermentation broth as fermentation continues. The continuous nature of such a process would have significant cost advantages over the now used batch system. An essential prerequisite for such a continuous system is the ability of the protein to be expressed in a solubilized form. Further, with respect to the first aspect of the present invention, it should be noted that solubilization of the protein when expressed could also potentially allow for the production of the toxin in a form as free from the structural proteins of the microorganism as possible. Under either scenario, the protein could then be converted to an insoluble preparation using methods well known to those skilled in the art, such as by acid precipitation or other methods, and utilized in the necessary insoluble form against the target insects. Other advantageous uses of this aspect of the present invention will become apparent to those skilled in the art.

In a second aspect, the invention pertains to nucleic acid fragments coding for insecticidal proteins having less haemolytic activity than the protein encoded by the wild type 27 kDa *Bacillus thuringiensis* var. israelensis gene. The removal or lessening of haemolytic activity has clear advantages, including minimization of any potential mammalian toxicity problems as well as minimization of public concern over the use of this protein in the environment, both of which are often problems and concerns concommitant with the use of agents that show haemolytic tendencies. However, as a practical matter, one skilled in the art would recognize that only under certain select conditions would the haemolytic activity of the subject wild type protein actually translate into a mammalian toxicity problem.

In a third aspect, the invention pertains to nucleic acid fragments coding for insecticidal proteins having a greater expression potential in cells containing significant amounts of phosphatidate-type toxin receptors than the protein encoded by the wild type 27 kDa *Bacillus thuringiensis* var. israelensis gene. Preferably, the cells containing significant amounts of phosphatidate-type toxin receptors are *E. coli* cells. This discovery permits effective production of the insecticidal protein in a number of cells, including *E. coli* which is one of the most conveniently employed and manipulated organisms presently known to man.

The various changes which can be made in the nucleic acids of the wild type gene to confer on the protein encoded thereby the desirable characteristics noted above have been identified herein with reference to the charge requirements of the encoded amino acids. For the purposes of the subject invention, the following amino acids are considered to possess the following charges:

| | |
|---|---|
| Positively charged amino acids | = Arg, Lys and His; |
| Negatively charged amino acids | = Glu and Asp; |
| Neutral amino acids | = Ala, Asn, Cys, Gly, Gln, Ile, Leu, Met, Phe, Pro, Ser, Thr, Trp, Tyr and Val |

The specific nucleotide changes in the wild type gene needed to produce the amino acid changes specified herein and the method for doing so will be readily apparent to the skilled artisan by reference to the examples provided therein and to the general body of knowledge in the art. See, for example, Oliver et al., "A Dictionary of Genetic Engineering", Appendix 5, pg. 152 (Cambridge University Press, Cambridge, England 1985).

As indicated above, within the constraints of the charge changes specified by the present invention, a number of suitably charged or uncharged, as the case may be, amino acid alternatives exist. Preferably amino acids within these alternatives, however, would be those which, except for the indicated charge change, possess minimal differences in physical and chemical properties from the target wild type amino acids. Such physical and chemical properties include polarity, hydrophobicity and conformational effects. For example, with the first aspect of the invention, one of the preferable amino acid substitutions for arginine at amino acid position 25, within the constrants of the specified charge changes, would be alanine. Other than the effects attributable to the charge change, the chemical and physical properties of alanine are such that polarity, hydrophobicity and conformation effects are minimized. The specific physical and chemical properties of the various amino acids are well documented and known to those skilled in the art. See, for example, Dickerson, R. E. and Geis, I., *The Structure and Action of Proteins* (Benjamin/Cummings Publishing Co., Menlo Park, Calif., 1969); Lehninger, A. L., *Biochemistry,* 2nd ed., pp. 72–76 (Worth Publishers, New York, N.Y., 1975); Darnell, J., Lodish, H. and Baltimore, D., *Molecular Cell Biology,* p. 54 (Scientific American Books, 1986).

As the present invention illustrates, specified amino acid substitutions can result in different desireable changes in the properties of the protein. For example, the replacement of glutamic acid at position 45 by alanine yields a protein with normal insecticidal activity but significantly reduced haemolytic activity, whereas replacement of arginine with alanine at either position 25 or 30 yields a protein which is produced in soluble form but which retains normal insecticidal activity. Thus the present invention also includes combinations of the substitution covered by the various aspects of the invention. The substitutions from the different aspects may separately confer different properties on the protein, but together will result in a mutant protein which possesses the combined properties of each of the different aspects. As an example, a nucleic acid fragment containing both an arginine to alanine mutation at position 25 and a glutamic acid to alanine mutation at position 45 of the wild type gene would be expected to yield a soluble protein product with significantly reduced haemolytic activity and normal insecticidal activity. The preferred nucleic acid fragments containing multiple mutations include those where the encoded protein contains (i) both a mutation from arginine to alanine at position 25 and glutamic acid to alanine at position 45 of the wild type gene and (ii) both a mutation from arginine to alanine at position 30 and glutamic acid to alanine at position 45 of the wild type gene.

The proteins encoded by the nucleic acid fragments of the subject invention may, other than with respect to any of the specified mutations which have been made, have either sequence homology (the same amino acid sequence, as defined above) or substantial sequence homology (an amino acid sequence substantially similar, as defined above) to the amino acid sequence shown in FIG. 1. Preferably the proteins are otherwise homologous thereto. Substantial similarity denotes herein that the number of amino acid substitutions, other than the substitutions directed to the specified mutations, are less than about 20%, more preferably less than about 10%, most preferably less than about 5% of the total number of amino acids in the protein. Of course, as one skilled in the art would recognize, within that numerical range, greater numbers of amino acid substitutions would be acceptable where physical and chemical property differences between the substituted amino acids and the wild type amino acids are minimized.

The proteins encoded by the present nucleic acid fragments are insecticidal, particularly mosquitocidal. Examples of the mosquitoes against which the proteins are effective include, but are not limited to, *Aedes albopictus, Aedes aegypti, Anopheles gambiae* and Culex. The control of Aedes and Anopheles mosquitoes is particularly important since these mosquitoes carry the potentially life-threatening diseases yellow fever and malaria, respectively, in certain areas of the world. A preferably target mosquito is *Aedes aegypti.*

The present invention also pertains to microorganisms containing the novel nucleic acid fragments described herein, and the use of these nucleic acid fragments to modify the properties or characteristics of microorganisms. In addition, the subject invention is directed to chimeric genes capable of expression in a microorganism or a plant cell comprising (1) a nucleic acid fragment in accordance with the present invention which encodes an insecticidal protein and (2) a nucleic acid fragment from a different source, and to microorganisms or plant cells containing such chimeric genes and plant tissues, seeds and plants which contain chimeric genes in one or more of their cells, as well as the use of these chimeric genes to modify the properties or characteristics of microorganisms, plant cells, plant tissues, plant seeds and/or plants. Preferably, the nucleic acid fragment from a different source is a promoter.

As one skilled in the art would recognize, the use of certain insecticidal nucleic acid fragments of the present invention may in fact necessitate the employ of a promoter from a different source. The particular promoter utilized must be recognized by the microorganism or the plant cell; that is, it must be capable of facilitating the transcription of the gene into mRNA by the RNA polymerase enzyme of the microorganism or plant cell.

Where expression in a microorganism is desired, a preferable microorganism is *Escherichia coli* or blue green algae. A number of other microorganisms, particularly other prokaryotes or lower eukaryotes such as fungi may be employed. Exemplary prokaryotes include Enterobacteriaceae such as Escherichia, Erwinia, Shigella, Salmonella and Proteus; Bacillacea; Rhizobiaceae, such as Rhizobium and Agrobacterium; Spirillaceae, such as Zymomonas, Serratia, Aeromonas, Vibrio, Desulfovibrio, Spirillum; Lactobacillaceae; Pseudomonadaceae, such as Pseudomonas and Acetobacter; Azotobacteraceae; Nitrobacteraceae; and Cyanophyta (blue green algae). Illustrative eukaryotes include algae such as Rhodophyta, Phaeophyta, Chlorophyta; fungi, such as Phycomycetes and Ascomycetes, which includes yeast such as Saccharomyces and Schizosaccharomyces; Basidiomycetes yeast such as Rhodotorula, Aureobasidium and Sporobolomyces; and mycorrhizal fungi.

Promoters suitable for microorganisms herein as well as other regulatory sequences which aid in gene expression (such as enhancers) in microorganisms will be readily apparent to those skilled in the art. See, for example, Old et al., "Principles of Gene Manipulation", Carr et al., eds. (Blackwell Scientific Publications, 1985); Rosenburg et al., *Ann. Rev. of Genetics,* 13: 319 (1979); European Patent Application Nos. 193,259 and 142,924; Vaeck et al., *Nature,* 328: 33 (1987); and Fishchhoff et al., *Biotechnology,* 5: 807 (1987). Other suitable promoters will be apparent to those skilled in the art.

Suitable plant cells for expression of the present chimeric genes, as well as promotors and other regulatory sequences which aid in such expression, are described in European Patent Application Nos. 193,259 and 142,924; Rosenburg et al., *Ann. Rev. of Genetics,* 13: 319 (1979); Vaeck et al., *Nature,* 328: 33 (1987); and Fishchhoff et al., *Biotechnology,* 5: 807 (1987). Other suitable plant cells and promoters will be apparent to those skilled in the art.

General genetic engineering procedures can be utilized to effect a transformation of microorganisms and plant cells with the novel nucleic acid fragments and/or chimeric genes such as those described in Maniatis et al., "Molecular Cloning: A Laboratory Manual" (Cold Spring Harbor, 1982) and European Patent Application Nos. 193,259 and 142,924. The modification of properties or characteristics sought is the conference of insecticidal properties or characteristics not otherwise possessed by the microorganisms, plant cells, plant tissues, plant seeds and/or plants.

Insecticidal compositions comprising an insecticidal amount of the aforementioned proteins and methods for controlling insects comprising applying to the locus to be protected an insecticidal amount of such proteins, are also within the ambit of the present invention.

In use, isolated proteins or microorganisms or plant cells (including plant tissues, plant seeds and/or plants) containing such proteins are applied to the locus (area) to be protected. The aforementioned protein or protein-containing microorganisms or cells are considered to be the active insecticidal ingredient in any insecticidal composition herein. The locus to be protected includes, for example, the habitat of the insect pests, growing vegetation or an area where vegetation is to be grown, stored, transported or otherwise handled, as appropriate. To isolate the proteins, the microorganisms or plant cells may be lysed using conventional means such as enzymatic degradation or detergents or the like, and the protein removed and purified by standard techniques such as chromatography, extraction, electrophoresis, or the like. Alternatively, the microorganisms or plant cells may be harvested and then dried and applied, or the microorganisms, plant cells, plant tissue, plant seeds and/or plants may be applied intact and alive. Other variations will be apparent to those skilled in the art.

The isolated proteins, the harvested and dried or the live protein-containing microorganisms or plant cells may be employed alone or as compositions, as noted above. The following formulations would be suitable.

For application, a protein or protein-containing cells or microorganisms of the present invention ordinarily is applied most effectively by formulating it with a suitable carrier or surface-active agent, or both. The invention, therefore, also includes insecticidal compositions comprising an inert carrier or surface-active agent, or both, and as an active ingredient at least one protein of the invention. The invention also provides a method of combatting insects at a locus, which comprises applying to the locus a protein of the invention or an insecticidal composition thereof.

The term "carrier" as used herein means an inert solid or liquid material, which may be inorganic or organic and of synthetic or natural origin, with which the protein or protein-containing cells or microorganisms are mixed or formulated to facilitate its application to the plant, seed, soil or other object to be treated, or to its storage, transport and/or handling facility. Any of the materials customarily employed in formulating insecticides, i.e., horticulturally acceptable adjuvants, are suitable.

Suitable solid carriers include, but are not limited to, natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; natural and synthetic resins such as, for example, coumarone resins, polyvinyl chloride and styrene polymers and copolymers; waxes such as, for example, beeswax, paraffin wax; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as toluene and xylene; and petroleum fractions such as kerosene and light mineral oils.

As used herein, the surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferable sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25–75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted inh the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agent, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts maybe dissolved in the carrier to assist in preventing sedimentation or as antifreeze agents for water.

Of potential interest in current practice are the water-dispersible granular formulations. These are in the form of dry, hard granules that are essentially dust-free, and are resilient to attrition on handling, thus minimizing the formation of dust. On contact with water, the granules readily disintegrate to form stable suspensions of the particles of active material. Such formulations contain 90% or more by weight of finely divided protein or protein-containing cells or microorganisms, 3–7% by weight of a blend of surfactants, which act as wetting, dispersinhg, suspending and binding agents, and 1–3% by weight of a finely divided carrier, which acts as a resuspending agent.

Aqueous dispersions and emulsions, for example, compositions obtained by diluting a wettable powder or a concentrate according to the invention with water, also lie within the scope of the present invention. Such emulsions may be of the water-in-oil or of the oil-in-water type, and may have thick, paste-like consistency.

It is evident from the foregoing that this invention contemplates compositions containing as little as about 0.0001% by weight to as much as about 99% by weight of a protein or protein-containing cells or microorganisms of the invewntion as the active ingredient.

The compositions of the invention may also contain other ingredients, for example, other compounds possessing insecticidal, fungicidal or other biocidal properties, as are appropriate to the intended purpose. Herbicides or fertilizers may also be additionally employed to provide further advantages or benefits.

The protein of the present invention is, of course, applied in an amount sufficient to effect the desired action. This dosage is dependent upon many factors, including the purity of the subject protein and/or the cells or microorganism(s) harboring the protein to be applied, the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected, i.e., the dosage which the insect contacts, is of the order of 0.001 to 0.5% based on total weight, though under some circumstances the effective concentration will be as little as 0.0001% or as much as 2%, on the same basis.

In practice, some of the insects feed on the insecticidal protein in the protected area, that is, the area where the isolated protein, or the harvested and dried proteinh-containing microorganisms or plant cells either alone or in a composition, or the intact and alive insecticidal nucleic acid-carrying microorganisms, plant cells, plant tissues, plant seeds and/or plants have been applied. In such a situation, the insect ingests some of the insecticidal protein and suffers death or damage.

The present invention is further described by the following Examples. These Examples are illustrative only and are not to be construed as limiting the scope of the invention. All molecular weights given in the Examples refer to appropriate weight average molecular weight based on the estimated weight of polyacrylamide gel samples.

EXAMPLES

General Procedures—Materials and Methods

The strains of *E. coli* utilized as cloning hosts for both the wild type 27000 Da δ-endotoxin *Bacillus thuringiensis* var. israelensis gene and the mutant derivatives were *E. coli* TG1 (K12, α(lac-pro), supE, thi, hsdD5/F'traD36, proA+B+, lacI$^q$, lacZΔM15), available from Dr. T. J. Gibson, MRC Laboratory of Molecular Biology, Cambridge, England and described in Gibon, T. J. Ph.D. Thesis, University of Cambridge, "Studies on the Epstein-Bar Virus Genome" (1984), and *E. coli* BMH 71-18 A9lac-proAB), thi, supE, F'lacI$^1$, lacZΔM15, proA+B+ mutL, available from Dr. G. Winter, MRC Laboratory of Molecular Biology, Cambridge, England and described in Kramer et al., *Nucleic Acids Res.*, 12: 9441–9456 (1984). *B. subtilis* 168 Sueoka trpC2, available from Dr. T. Leighton, Department of Microbiology and Immunology, University of California, Berkeley, Ca. 94720, and described in Leighton et al., *J. Biol. Chem.*, 246: 3189–3195 (1971), and *B. subtilis* MB24 metc3, rif, trpC2, available from Dr. P. Piggot, Department of Microbiology and Immunology, Temple University School of Medicine, Philadelphia, Pa. 19140, were also used as cloning hosts for preparation of the wild type 27000 Da δ-endotoxin and the mutant derivatives.

Plasmids Camtaq 11 and Cambtaq 6 were employed as cloning vectors. Plasmid Camtaq 11 has been previously described in Ward et al., *J. Mol biol.*, 191: 1–11 (1986) and Ward et al., *J. Mol. Biol.*, 191: 13–22 (1986). Plasmid Cambtaq 6 is similar to Camtaq 11 except that the 1.2 kb TaqI fragment harbouring the δ-endotoxin gene is oriented in the opposite direction.

Phage vectors M13tg130 and M13tg131 (available from Amersham PLC, Amersham, Buckinghamshire, England) were used during the construction and sequence analysis of the mutants.

Plasmid pUC19, used as a cloning vector, has been previously described (Yannisch-Perrson et al., *Gene* 33: 103–119 (1985)). The 17 base pair oligonucleotides used in this study were synthesised by the B-cyanoethyl phosphoamidite method usinjg a Biosearch 8750 four column DNA synthesiser from Biosearch, Inc., 2980 Kerner Blvd., San Rafael, Calif., U.S.A.

Restriction enzymes were otained from New England Biolabs, Bethesda Research Laboratories, Bethesda, Md., U.S.A. and were used in the medium salt buffer discussed by Maniatis et al., in "Molecular Cloning: A Laboratory Manual" (Cold Spring Harbor, 1982). T4 DNA Ligase (purchased from New England Biolabs) and the Klenow fragment of DNA polymerase (both readily available from a number of well-known sources) were employed. 32-P-ATP (3000 Ci/mole) and 35-S-dATP were obtained from Amersham PLC.

SDS polyacrylamide gels were prepared as described previously in Laemmli, *Nature* (London), 227: 680–685 (1970).

EXAMPLE 1

Site-Directed Mutagenesis of the *Bacillus thuringiensis* subsp. israelensis 27 kDa δ-Endotoxin Gene and Expression of the Resultant Mutated Nucleic Acid Fragments The use of an M13 phage vector as a source of single-stranded DNA template has been previously described in Gillam et al., *Gene*, 8: 81–97 (1979), Gillam et al., *Gene*, 8: 99–106 (1979), and Winter et al., *Nature* (London), 299: 756–758 (1982). A 790 bp or 425 bp PstI fragment, containing a portion of the δ-endotoxin gene and either 5' or 3' flanking regions were generated using a PstI site in the 27 kDa δ-endotoxin Bacillus thuringiensis var. israelensis genome and a PstI site in the polylinker of the cloning vector pUC12 (described by Messing, *J. Meths. Enzymol.*, 101: 20–78 (1983). These two fragments were purified and ligated into the PstI site of phages M13tg130 in both orientations, and recombinants producing single stranded DNA (ssDNA) containing the non-coding δ-endotoxin strand was used as a template to generate mutants.

The synthetic oligonucleotides utilized in obtaining the mutants, together with the amino acid changes which the oligonucleotides directed were as follows:

| | |
|---|---|
| (i) | 5'-GTAATAACCGCTGCTGT-3'<br>(Arg25→Ala25)<br>(nucleotide positions 73–75); |
| (ii) | 5'-TCCTCAACAGCTAATGT-3'<br>(Arg30→Ala30)<br>(nucleotide positions 88–90); |
| (iii) | 5'-TTTGGATCCGCAACACG-3'<br>(Glu32→Ala32)<br>(nucleotide positions 94–96); |
| (iv) | 5'-TCATTTGGAGCCTCAAC-3'<br>(Asp33→Ala33)<br>(nucleotide positions 97–99); |
| (v) | 5'-TTATTGATTGCATTTGG-3'<br>(Glu36→Ala36)<br>(nucleotide positions 106–108); |
| (vi) | 5'-TTATCAATTGCGTTAAT-3'<br>(Glu45→Ala45)<br>(nucleotide positions 133–135); |
| (vii) | 5'-TTATCAATATCGTTAAT-3'<br>(Glu45→Asp45)<br>(nucleotide positions 133–135); |
| (viii) | 5'-TTCGGATTAGCAATTTC-3'<br>(Asp47→Ala47) |

-continued

| | |
|---|---|
| | (nucleotide positions 139–141); |
| (ix) | 5'-TCACCAAAAGCTGTAGA-3' |
| | (Asp72→Ala72) |
| | (nucleotide positions 214–216); |
| (x) | 5'-CGTAGGGCAGCACCAAA-3' |
| | (Asp75→Ala75) |
| | (nucleotide positions 223–225); |
| (xi) | 5'-ATACTAAGGCTAGGGC-3' |
| | (Arg78→Ala78) |
| | (nucleotide positions 232–234); |
| (xii) | 5'-ATACTAAATTTTAGGGC-3' |
| | (Arg78→Lys78) |
| | (nucleotide positions 232–234); |
| (xiii) | 5'-TCTAAACCTGCTGGCAT-3' |
| | (Lys83→Ala83) |
| | (nucleotide positions 247–249); |
| (xiv) | 5'-TTTGCGATTGCTAAACC-3' |
| | (Glu86→Ala86) |
| | (nucleotide positions 256–258); |
| (xv) | 5'-ACATTTTGAGCAACATA-3' |
| | (Asp102→Ala102) |
| | (nucleotide positions 304–306); |
| (xvi) | 5'-CTAAGACTGCATTAATC-3' |
| | (Lys118→Ala118) |
| | (nucleotide positions 352–354); |
| (xvii) | 5'-TTAACACTGCTAAGACT-3' |
| | (Glu121→Ala121) |
| | (nucleotide positions 361–363); |
| (xviii) | 5'-ATACAGTTGCTAACACT-3' |
| | (Lys124→Ala124) |
| | (nucleotide positions 370–372); |
| (xix) | 5'-TATATTGAGCTATTACA-3' |
| | (Asp137→Ala137) |
| | (nucleotide positions 419–421); |
| (xx) | 5'-CTTCATTTGCTTGAGTA-3' |
| | (Lys154→Ala154) |
| | (nucleotide positions 460–462); |
| (xxi) | 5'-TCCATGCTGCATTTTTT-3' |
| | (Glu156→Ala156) |
| | (nucleotide positions 466–468); |
| (xxii) | 5'-CAGTTTCCGCGCCCCAG-3' |
| | (Lys163→Ala163) |
| | (nucleotide positions 487–489); |
| (xxiii) | 5'-TAGCAGTTGCCTTGCCC-3' |
| | (Glu164→Ala164) |
| | (nucleotide positions 490–492); |
| (xxiv) | 5'-CTTTAATTGCAAAACCA-3' |
| | (Glu196→Ala196) |
| | (nucleotide positions 586–588); |
| (xxv) | 5'-TGCTGATACTGCAATTTC-3' |
| | (Lys198→Ala198) |
| | (nucleotide positions 592–594); |
| (xxvi) | 5'-CTTGTTCCGCTACTGCT-3' |
| | (Lys203→Ala203) |
| | (nucleotide positions 607–609); |
| (xxvii) | 5'-T.AAACTTGTGCCTTTAC-3' |
| | (Glu204→Ala204) |
| | (nucleotide positions 610–612); |
| (xxviii) | 5'-TCGCAGATGCTTGAATT-3' |
| | (Asp213→Ala213) |
| | (nucleotide positions 637–639); |
| (xxix) | 5'-GTGCAAATGCCAAAGAT-3 |
| | (Lys225→Ala225) |
| | (nucleotide positions 673–675); |
| (xxx) | 5'-TAGTAAGAGCTGCAATT-3' |
| | (Glu240→Ala240) |
| | (nucleotide positions 718–720). |

To create the mutants, ten picomoles of each of the above kinased oligonucleotide were annealed to 1 μg of the single-stranded template, using the procedure described by Carter, P. et al., in "Oligonucleotide Site-Directed Mutagenesis in M13" (Anglian Biotechnology Ltd., England, 1985), with the exception that M13 primer was omitted from the annealing reaction. Plaques resulting from the transfection of *E. coli* BMH 71-19 mutL were grown as infected colonies and screened usinhg 32-P labelled oligonucleotide as described in Carter, P. et al., (above). After plaque purification of hybridization positive colonies, single plaques were picked and used to inoculate cultures of *E. coli* TG1. The inoculated *E. coli* TG1 cultures were centrifuged and ssDNA was prepared from the supernatant and replicative form DNA (RF DNA) (described by Bankier, A. et al., in "Techniques in the Life Sciences", Vol. B508, pp. ff1–34 (Elsevier, Amsterdam, 1983) was isolated from the cell pellet following the procedures in Birnboim et al., Nucleic Acids Res., 7: 1513–1523 (1979).

The ssDNA from each of the inoculated cultures was used for dideoxy sequencing analysis as described in Sanger et al., *Proc. Natl. Acad. Sci. U.S.A.*, 74: 5643–5468 (1977) and Bankier, A. et al., in "Techniques in the Life Sciences", Vol B508, pp. 1–34 (Elsevier, Amsterdam, 1983).

The RF DNA carrying the desired mutations was used to construct a complete δ-endotoxin gene containing the required condon change inserted in plasmids Camtaq 11 or Cambtaq 6.

Specifically, RF DNA harbouring mutationhs introduced by the oligonucleotides (i) through (xxx) described above were restricted with PstI, and the 790 bp or 425 bp fragments were gel purified as described previously in Dretzen et al., *Anal. Biochem.*, 112: 295–298 (1981), with the exception that the DNA was electrophoresed onto Schleicher and Schuell NA45 paper from Schleicher and Schuell, Inc., Keene, N.H. 03431, U.S.A. The fragments were then ligated into a gel purified 5.9 kb or 6.15 kb PstI fragment derived from Camtaq 11 or Cambtaq 6, respectively, (described inh Ward et al., *J. Mol. Biol.*, 191: 1–11 (1986); Ward et al., *J. Mol. Biol.*, 191: 13–22 (1986)) resulting in a chimeric plasmid consisting of pUC12 (described in Messing, *Meths. Enzymol.*, 101: 20–78 (1983) and found in Camtaq 11 and Cambtaq 6), pC194 (described in Horinouchi et al., *J. Bacteriol.*, 150: 812–825 (1982) and found in Camtaq 11 and Cambtaq 6) and either a 480 bp or a 715 bp PstI-TaqI mutant fragment of var. israelensis DNA. For brevity sake, the mutants are referred to herein inh an abbreviated fashion using, for example, the designation Ala45 to indicate the presence of a 27 kDa δ-endotoxin gene containing nucleotide change(s) that resulted in an amino acid change at position 45 from glutamic acid in the wild type protein to alanine in the mutant protein.

*E. coli* was utilized initially as the cloning host. Plasmid DNA isolated from *E. coli* recombinants was analyzed by restriction enzyme digestion, and the constructs harbouring complete mutant δ-endotoxin genes were used to transform *B. subtilis* in accordance with the methods described in Chang et al., *Mol. Gen. Genet.*, 168: 111–115 (1979). DNA isolated from the resulting *B. subtilis* recombinants was restricted, and used to generate ssDNA template to resequence the region of the gene containing the mutation.

Recombinant *B. subtilis* cells harbouring chimeric plasmids containing the mutant δ-endotoxin genes were grown as previously described. See, Ward et al., *J. Mol. Biol.*, 191: 1–11 (1986); Ward et al., *J. Mol. Biol.*, 191: 13–22 (1986); and Haider et al., *Molec. Microbiol.*, 1: 59–66 (1987). *B. subtilis* recombinants harbouring the changes directed by synthetic oligonucleotides (i) through (xxx) were harvested at various stages of sporulation, resuspended in Solution I (described in Birnboim et al., *Nucleic Acids Res.*, 7: 1513–1523 (1979)) containing 2 mg/ml lysozyme for 10 minutes at 20° C., and then lysed by sonication as described previously in Ward etr al., *FEBS Letts.*, 175: 377–781 (1984). Cell lysates from the *B. subtilis* cells were then analysed by polyacrylamide gel electrophoresis and immunoblotting as previously described. See, Towbin et al., *Proc. Nat. Acad. Sci.*, 76: 4350–4354 (1979); Hawkes et al., *Anal. Biochem.*, 119: 142–147 (1982).

To determine the amount of protein expressed, the following procedures were used. Where inclusions were present, the inclusions were isolated from the spore-crystal mixtures using sucrose density gradient centrifugation and the concentration of protein in the inclusions were determined by the method of Lowry et al., *J. Biol. Chem.*, 193: 265–275 (1951). Assessments of the amount of protein in soluble form were made by comparing the intensity of protein bands reacting with antibody specific for the wild type 27 kDa *Bacillus thuringiensis* var. israelensis gene product. The results are reported in Tables IA and IB below.

Table IA shows the ability of the mutant to form inclusions and, in qualitative terms, the amount of 27 kDa protein observed at sporulation Stage VI, the final stage of protein synthesis.

Table IB shows quantitatively the amount of protein produced by various mutants at Stages III and VI of sporulation. The values given are in terms of estimated percent of dry weight of bacterial cultures. For comparison purposes, it should be noted that the wild type level of expression at Stage III is 5%, and at Stage VI is 10%.

TABLE IA

| Mutant | Ability To Form Inclusions | Amount of 27 kDa Protein Observed |
|---|---|---|
| Ala25 | none visible | same as wild-type |
| Ala30 | none visible | same as wild-type |
| Ala32 | same as wild-type | same as wild-type |
| Ala33 | same as wild-type | same as wild-type |
| Ala36 | same as wild-type | same as wild-type |
| Ala45 | same as wild-type | same as wild-type |
| Asp45 | same as wild-type | same as wild-type |
| Ala47 | same as wild-type | same as wild-type |
| Ala72 | same as wild-type | same as wild-type |
| Ala75 | same as wild-type | same as wild-type |
| Ala78 | much smaller than wild-type | much less than wild-type |
| Lys78 | much smaller than wild-type | same as wild-type |
| Ala83 | same as wild-type | same as wild-type |
| Ala86 | same as wild-type | same as wild-type |
| Ala102 | same as wild-type | same as wild-type |
| Ala118 | same as wild-type | same as wild-type |
| Ala121 | same as wild-type | same as wild-type |
| Ala124 | much smaller than wild-type | same as wild-type |
| Ala137 | same as wild-type | same as wild-type |
| Ala154 | same as wild-type | same as wild-type |
| Ala156 | same as wild-type | same as wild-type |
| Ala163 | same as wild-type | same as wild-type |
| Ala164 | same as wild-type | same as wild-type |
| Ala196 | same as wild-type | same as wild-type |
| Ala198 | same as wild-type | same as wild-type |
| Ala203 | much smaller than wild-type | same as wild-type |
| Ala204 | much smaller than wild-type | same as wild-type |
| Ala213 | same as wild-type | same as wild-type |
| Ala225 | same as wild-type | same as wild-type |
| Ala240 | much smaller than wild-type | same as wild-type |

TABLE IB

| Mutant | Level of Expression of 27 kDa Protein | |
|---|---|---|
| | Stage III | Stage VI |
| Ala25 | 5% | 10% |

TABLE IB-continued

| Mutant | Level of Expression of 27 kDa Protein | |
|---|---|---|
| | Stage III | Stage VI |
| Ala30 | 5% | 10% |
| Ala78 | 5% | 2% |
| Ala124 | 5% | 10% |
| Ala203 | 5% | 10% |
| Ala204 | 5% | 10% |
| Ala240 | 5% | 10% |

EXAMPLE 2

Effect of Proteins Produced by the Novel Nucleic Acid Fragments Derived from the subsp. israelensis 27 kDa Gene on *E. coli* Growth, and the Ability of Such Proteins to Bind to Phosphatidyl Choline In Vitro Recombinant *E. coli* cells harbouring chimeric plasmids containing the mutation from Glu45 to Ala45 were cultured in the presence of 0.5 mM IPTG as previously described in Ward, E. S., Ph.D. Thesis, University of Cambridge, "Molecular Genetics of an Insecticidal δ-endotoxin from *Bacillus thuringiensis* var. israelenis" (1988), and their growth patterns observed and compared to the *E. coli* cells harbouring the wild type gene. The cells were harvested after 40 hours, and were lysed using the same method as was used for *B. subtilis*, with the exception that the incubation in Solution I was carried out at 0° C.

Cell lysates from *E. coli* cells were then analysed by polyacrylamide gel electrophoresis and immunoblotting as previously described. See, Towbin et al., *Proc. Nat. Acad. Sci.*, 76: 4350–4354 (1979); Hawkes et al., *Anal. Biochem.*, 119: 142–147 (1982).

A determination of binding to phosphatidyl choline liposomes (PC Binding) was also made, since it has been postulated that binding of the protein toxin to phosphatidyl choline present in the cell plasma membrane is one important factor in the toxin's cytolytic process. The PC binding determination was made using the procedures reported in Ellar et al., Biochemistry, Genetics and Mode of Action of *Bacillus Thuringiensis* δ-endotoxins, in "Molecular Biology of Microbial Differentiation", pp. 230–240 (American Society for Microbiology, Washington, D.C., 1985). It should be noted for comparison purposes that the wild type 27 kEa gene product does exhibit PC binding.

The results are reported in Table II below.

TABLE II

| Mutant | Amount of 27 kDa Protein Observed | Effect on Bacterial Growth | PC Binding |
|---|---|---|---|
| Ala45 | same as wild-type | no deleterious effect | No |

EXAMPLE 3

In vitro Haemolytic Assays and Phosphatidyl Choline Binding Assays of Proteins Produced by Novel Nucleic Acid Fragments Derived from the subsp. israelenis 27 kDa Gene Lysates of or inclusions purified from *B. subtilis* recombinants carrying the 27 kDa gene mutated as described in Example 1 were assayed for haemolysis in vitro using human or rabbit erythrocytes following the procedures set forth in Thomas et al., *J. Cell Sci.*, 60: 181–197 (1983) and Thomas et al., *FEBS letts.*, 145:

362–368 (1983). The inclusion protein was solubilised in 50 mM $NA_2$ $CO_3$—HCl, pH 10.5, in the presence of a 1/10 volume of *A. aegypti* gut extract prior to application. A determination of binding to phosphatidyl choline liposomes (PC Binding) was also made. The PC binding tests were carried out as described above. The designation "---" indicates that the particular test was not run.

The results are given in Table III below.

TABLE III

| Mutant | Haemolytic Activity | PC Binding |
|---|---|---|
| Ala25 | same as wild-type | — |
| Ala30 | same as wild-type | — |
| Ala32 | same as wild-type | — |
| Ala33 | same as wild-type | — |
| Ala36 | same as wild-type | — |
| Ala45 | much less than wild-type (12% of wild-type) | no |
| Asp45 | same as wild-type | — |
| Ala47 | same as wild-type | — |
| Ala72 | same as wild-type | — |
| Ala75 | same as wild-type | — |
| Ala78 | much less than wild type (qualitative) | — |
| Lys78 | same as wild-type | — |
| Ala83 | same as wild-type | — |
| Ala86 | same as wild-type | — |
| Ala102 | same as wild-type | — |
| Ala118 | same as wild-type | — |
| Ala121 | same as wild-type | — |
| Ala124 | same as wild-type | yes |
| Ala137 | same as wild-type | — |
| Ala154 | no haemolytic activity (0% of wild-type)* | no |
| Ala156 | same as wild-type | — |
| Ala163 | no haemolytic activity (0% of wild-type)* | no |
| Ala164 | less than wild-type (50% of wild-type) | no |
| Ala196 | same as wild-type | — |
| Ala198 | same as wild-type | — |
| Ala203 | same as wild-type | — |
| Ala204 | less than wild-type (25% of wild-type) | no |
| Ala213 | same as wild-type | no |
| Ala225 | no haemolytic activity (0% of wild-type) | no |
| Ala240 | same as wild-type | — |

*0% indicates that no haemolysis could be detected when the mutant polypeptide was used at a concentration of 60 μg/ml; for the wild-type protein, haemolysis could be detected at 7.5 μg/ml under the conditions of the assay.

EXAMPLE 4

In vivo Toxicity Assays and in vitro Phosphatidyl Choline Binding Assays of Proteins Produced by Novel Nucleic Acid Fragments Derived from the subsp. israelensis 27 kDa Gene Purified inclusions or lysates of recombinant *B. subtilis* cells were assayed for in vivo toxicity using 3rd instar *Aedes aegypti* larvae as described previously. Ward et al., *FEBS Letts.*, 175: 377–781 (1984). Table IV shows the toxicity characteristics of the mutant polypeptides in vivo. $LC_{50}$ values are in ng/ml after 24 hours of assay. The $LC_{50}$ of the wild-type protein is 125 ng/ml. The results of PC binding assays, carried out as described above, are also provided. The designation "---" indicates that the particular test was not run.

The results are reported in Table IV below.

TABLE IV

| Mutant | $LC_{50}$ Value | PC Binding |
|---|---|---|
| Ala25 | same as wild-type (qualitative) | — |
| Ala30 | same as wild-type (qualitative) | — |
| Ala32 | same as wild-type (qualitative) | — |
| Ala33 | same as wild-type (qualitative) | — |
| Ala36 | same as wild-type (qualitative) | — |
| Ala45 | same as wild-type 125 ng/ml | no |
| Asp45 | same as wild-type (qualitative) | — |
| Ala47 | same as wild-type (qualitative) | — |
| Ala72 | same as wild-type (qualitative) | — |
| Ala75 | same as wild-type (qualitative) | — |
| Ala78 | less activity than wild-type (>12000 ng/ml) | — |
| Lys78 | same as wild-type (qualitative) | — |
| Ala83 | same as wild-type (qualitative) | — |
| Ala86 | same as wild-type (qualitative) | — |
| Ala101 | same as wild-type (qualitative) | — |
| Ala118 | same as wild-type (qualitative) | — |
| Ala121 | same as wild-type (qualitative) | — |
| Ala124 | less activity than wild-type (qualitative) | yes |
| Ala137 | same as wild-type (qualitative) | — |
| Ala154 | less than wild-type (>1000 ng/ml) | no |
| Ala156 | same as wild-type (qualitative) | — |
| Ala163 | less than wild-type (500 ng/ml) | no |
| Ala164 | less than wild-type (500 ng/ml) | no |
| Ala196 | same as wild-type (qualitative) | — |
| Ala198 | same as wild-type (qualitative) | — |
| Ala203 | less than wild-type (qualitative) | — |
| Ala204 | less than wild-type (qualitative) | no |
| Ala213 | less than wild-type (1000 ng/ml) | no |
| Ala225 | less than wild-type (>1000 ng/ml) | no |
| Ala240 | less than wild-type (qualitative) | — |

What is claimed is:

1. A nucleic acid fragment comprising a nucleic acid sequence encoding a soluble insecticidal protein, wherein at least one of the positively charged amino acids selected from the group consisting of lysine, arginine, aspartate and glutamate is instead a negatively charged or neutral amino acid.

2. A nucleic acid fragment according to claim 1 wherein at least one of the positively charged amino acids is instead a neutral amino acid.

3. A nucleic acid fragment according to claim 2 wherein the neutral amino acid is alanine.

4. A nucleic acid fragment according to claim 3 wherein arginine 25 is instead alanine 25, arginine 30 is instead alanine 30, arginine 78 is instead alanine 78, or lysine 124 is instead alanine 124.

5. A nucleic acid fragment according to claim 4 wherein arginine 25 is instead alanine 25.

6. A nucleic acid fragment according to claim 4 wherein arginine 30 is instead alanine 30.

7. A nucleic acid fragment according to claim 4 wherein arginine 78 is instead alanine 78.

8. A nucleic acid fragment according to claim 4 wherein lysine 124 is instead alanine 124.

9. A nucleic acid fragment according to claim 1 which is a DNA fragment.

10. A nucleic acid fragment according to claim 1 wherein the molecular weight of the encoded solubilized insecticidal protein is about 27 kDa.

11. A microorganism selected from the group consisting of *Bacillus megaterium, Bacillus subtilis* and *Bacillus thuringiensis* containing a nucleic acid fragment according to claim 1.

* * * * *